United States Patent [19]

Tullis

[11] Patent Number: 4,904,582

[45] Date of Patent: Feb. 27, 1990

[54] NOVEL AMPHIPHILIC NUCLEIC ACID CONJUGATES

[75] Inventor: Richard H. Tullis, Leucadia, Calif.

[73] Assignee: Synthetic Genetics, San Diego, Calif.

[21] Appl. No.: 61,874

[22] Filed: Jun. 11, 1987

[51] Int. Cl.$^4$ .................... C12Q 1/68; C07H 15/12; G01N 33/566

[52] U.S. Cl. .......................... 435/6; 424/44; 435/172.3; 435/240.2; 435/243; 436/501; 536/27; 935/2; 935/4; 935/33; 935/34; 935/36; 935/77; 935/78

[58] Field of Search .............. 435/6, 172.3, 240.2, 435/243; 436/501; 424/44; 536/27; 935/2, 4, 33, 34, 36, 77, 78

[56] References Cited

U.S. PATENT DOCUMENTS

| | | | |
|---|---|---|---|
| 4,511,713 | 4/1985 | Miller et al. | 536/27 |
| 4,587,044 | 5/1986 | Miller et al. | 530/211 |
| 4,689,320 | 8/1987 | Kaji | 536/28 |
| 4,757,141 | 7/1988 | Fung et al. | 536/27 |

FOREIGN PATENT DOCUMENTS 2153356A 8/1985 United Kingdom .

OTHER PUBLICATIONS

Amasino "Acceleration of Nucleic Acid Hybridization Rate by Polyethylene Glycol," Anal. Biochem. 152, 304–307 (1986).

Tullis et al., "Specific Detection of Human and Rabbit Glucagon mRNA Using a Synthetic Oligodeoxynucleotide," in Biochem. Biophys. Res. Comm. (1980) 93:941–947.

Stephenson et al., "Inhibition of Rous Sarcoma Viral RNA Translation by a Specific Oligodeoxyribonucleotide," in Proc. Natl. Acad. Sci. U.S.A. (1978) 75(1): 280–288.

Tullis et al., "Oligonucleotides as Specific Translation Inhibitors," in J. Cellular Biochem. Supp. (1984) 8A:58.

Blake et al., "Inhibition of Rabbit Globin mRNA Translation by Sequence-Specific Oligodeoxyribonucleotides," in Biochemistry (1985) 24:6231–6138.

Barrett et al., "Inhibitory Effect of Complex Formation with Oligodeoxyribonucleotide Ethyl Phosphotriesters on Transfer Ribonucleic Acid Aminocylation," in Biochemistry (1974) 13(24):4897–4906.

Chollet et al., "Biotin-Labeled Synthetic Oligodeoxyribonucleotides: Chemical Synthesis and Uses as Hybridization Probes," in Nucl. Acids Res. (1985) 13(5):1529–1541.

Knorre et al., "Nucleotide and Oligonucleotide Derivatives as Enzyme and Nucleic Acid Targeted Irreversible Inhibitors," in Adv. Enzyme Regulation (1986) 1984:277–300.

Chu et al., "Derivatization of Unprotected Polynucleotides," in Nucl. Acids Res. (1983) 11(18):6513–6529.

Connolly et al., "Chemical Synthesis of Oligonucleotides Containing a Free Suphydryl Group and Subsequent Attachment of Thiol Specific Probes," in Nucl. Acids Res. (1985) 13(12):4485–4502.

Smith et al., "Synthesis of Oligonucleotides Containing an Aliphatic Amino Group at the 5' Terminus: Synthesis of Fluorescent DNA Primers for Use in DNA Sequence Analysis," in Nucl. Acids Res. (1985) 13(7):2399–2412.

Caruthers, "Gene Synthesis Machines: DNA Chemistry and its Uses," in Science (1985) 230:281–285.

Miller et al., "Solid-Phase Syntheses of Oligodeoxyribonucleoside Methylphosphonates," in Biochemistry (1986) 25:5092–5097.

Primary Examiner—Robert A. Wax
Attorney, Agent, or Firm—Bertram I. Rowland

[57] ABSTRACT

Novel oligonucleotide conjugates are provided, where oligonucleotides are joined through a linking arm to a hydrophobic moiety. The resulting conjugates are more efficient in membrane transport, so as to be capable of crossing the membrane and effectively modulating a transcriptional system. In this way, the compositions can be used in vitro and in vivo, for studying cellular processes, protecting mammalian hosts from pathogens, and the like.

19 Claims, No Drawings

NOVEL AMPHIPHILIC NUCLEIC ACID CONJUGATES

INTRODUCTION

Technical Field

The subject invention relates to specific polynucleotide binding polymers conjugated to solubility modifying moieties for inhibition of expression.

Background

There is a continuing interest and need for agents capable of modulating intracellular expression. The agents could have a profound capability of solving a variety of genetically associated problems. These agents, particularly complementary nucleic acid agents, could be used as antiviral agents to inhibit the expression of viral essential genes. The agents also could act as anti-neoplastic agents, reducing the rate of proliferation of cancer cells or inhibiting their growth entirely. These agents would act intracellularly binding to transcription products by a mechanism or mechanisms unknown, to inhibit the expression of a particular structural gene.

There has been substantial interest in this possibility and a number of experiments in culture have shown that there may be some promise to this approach. However, there are also numerous short-comings to the approaches that have been used previously. In order to provide for a useful agent for therapy, the agent should be effective at low concentrations, so as to allow for relatively low dosages when administered systemically. Secondly, agents should be relatively stable and resistant to degradation by the various nucleases. Thirdly, the agent should be very rapid once introduced into the cytoplasm and highly specific in binding to its complementary sequence, so as to avoid long incubation periods. Fourth, the agent should be able to penetrate the membrane. The agent should be effective at low concentrations to avoid high concentrations in the blood stream. Finally, adverse effects to the mammalian host should be minimized and the oligonucleotide agent should provide for a minimal immunogenic response. While various of these criteria may be compromised to different degrees, the agents which have been produced so far fall far short of agents which might find general use.

Relevant Literature

Use of relatively short probes to maximize selectivity while retaining high sensitivity to single base mismatches is suggested by Szostak, et al., *Methods Enzymol.* (1979) 68:419-429; Wu, *Nature New Biology* (1972) 236:198; Itakura and Riggs, *Science* (1980) 209:1401; Noyes, *J. Biol. Chem.* (1979) 254:7472-7475; Noyes et al., *Proc. Natl. Acad. Sci. USA* (1979) 76:1770-1774; Agarwal, et al., *J. Biol. Chem.* (1981) 256:1023-1028. Tullis, et al., *Biochem. Biophys. Res. Comm.* (1980) 93:941; Orkin et al., *J. Clin. Invst.* (1983) 71:775; Conner et al., *Proc. Natl. Acad. Sci. USA* (1983) 80:278; Piratsu et al., *New Eng. J. Med.* (1983) 309:284-287; Wallace et al., *Gene* (1981) 16:21.

There have been a number of reports on the use of specific nucleic sequences to inhibit viral replication. See for example, Zamecink and Stephenson, *Proc. Natl. Acad. Sci. USA* (1978) 75:280-284; Tullis et al., *J. Cellular Biochem. Suppl.* (1984) 8A:58 (Abstract); Kawasaki, *Nucl. Acids. Res.* (1985) 13:4991; Walder et al., *Science* (1986) 233:569-571; Zamecnik et al., *Proc. Nat'l. Acad. Sci., USA* (1986) 83:4143-4146.

Modified nucleic acids, such as triesters and methylphosphonates have also been shown to be effective in inhibiting expression. Miller et al., *Biochemistry* (1974) 13:4887-4895; Barrett et al., Ibid. (1974) 13:4897-4906; Miller et al., Ibid. (1977) 16:1988-1997; Miller et al., *Biochemistry* (1981) 20:1873-1880; Blake et al., *Biochemistry* (1985a, b) 24:6132 and 6134; Smith et al., *Proc. Nat'l. Acad. Sci. USA* (1986) 83:2787-91; Agris et al., *Biochemistry* (1986) 25:6268-6275; Miller et al., *Biochemistry* (1986) 25:5092-5097.

Modified nucleic acid sequences for enhancing binding to the complementary sequence are reported by Vlassov et al., *Adv. Eng. Reg.* 1986:301-320; Summerton *J. Theor. Biol.* (1979) 78:77-99; Knorre (1986) *Adv. Eng. Reg.* 1986:277-300.

Reduced immunogenicity of proteins conjugated to polyethyleneglycol is report by Tomasi and Fallow, WO86/04145 (PCT/U585/02572) and Abuchowski et al., *Cancer Biochem. Biophys.* (1984) 7:175-186. See also U.S. Pat. Nos. 4,511,713 and 4,587,044.

SUMMARY OF THE INVENTION

Novel nucleic acid conjugates are provided comprising a relatively short nucleic acid sequence complementary to a sequence of interest for modifying intracellular expression, a linking group, and a group which imparts amphiphilic character to the final product, usually more hydrophobic than hydrophilic, where hydrophobic includes amphiphilic. The nucleic acid moiety may include normal or other sugars, phosphate groups or modified phosphate groups or bases other than the normal bases where the modifications do not interfere with complementary binding of the sequence of interest. The compositions find use for inhibiting mRNA maturation and/or expression of particular structural genes, such as in neoplastic cells, of viral proteins in viral infected cells, and essential protein(s) of human and animal pathogens.

DESCRIPTION OF THE SPECIFIC EMBODIMENTS

The subject invention provides novel nucleic acid conjugates for inhibiting intracellular mRNA maturation and/or expression of a structural gene. Conjugates comprise a relatively short oligonucleotide sequence, a linking group, and a group which modifies the HLB (hydrophilic lipophilic balance) to provide an amphiphilic product product. The amphiphilic nature of the product aids in the transport of the conjugate across the cellular membrane and can provide additional advantages, such as increasing aqueous or liquid solubility of nucleic acid derivatives, e.g., use of an amphiphilic group to enhance water solubility of long chain methyl phosphonates and stabilizing normal nucleic acids to exonuclease digestion.

For the most part, compounds of this invention will have the following formula:

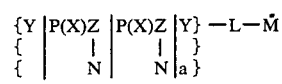

X is usually a pair of electrons, chalcogen (oxygen or sulfur) or amino, particularly NH;

Z is a naturally occurring or synthetic sugar residue linked at two of the 2', 3' and 5' hydroxyls of the five carbon sugars and at comparable sites for six carbon sugars, where the sugars will usually be ribose, or deoxyribose, or other 5 carbon or 6 carbon, particularly 5 carbon, sugars such as arabinose, xylose, glucose, or galactose;

N is any natural or unnatural base (purine or pyrimidine) capable of binding to and hybridizing with a natural purine or pyrimidine, the purines and pyrimidines may be the natural deoxyribose nucleoside purines and pyrimidines, such as adenine, cytidine, thymidine, guanidine or other purines and pyrimidines, such as uracil, inosine, and the like.

L is a linking group which is derived from a polyvalent functional group having at least 1 atom, not more than about 60 atoms other than hydrogen, usually not more than about 30 atoms other than hydrogen, having up to about 30 carbon atoms, usually not more than about 20 carbon atoms, and up to about 10 heteroatoms, more usually up to about 6 heteroatoms, particularly chalcogen, nitrogen, phosphorous, etc., non-oxo-carbonyl (carboxy carbonyl), oxo-carbonyl (aldehyde or ketone), or the sulfur or nitrogen equivalents thereof, e.g., thiono, thio, imidyl, etc. as well as disulfide, amino, diazo, hydrazino, oximino, etc., phosphate, phosphono, and the like.

M is a solubility modifying moiety which imparts amphiphilic character to the molecule, particularly hydrophobic with phosphates and amphiphilic with phosphonates, which will have a ratio of carbon to heteroatom of at least 2:1, usually at least 3:1, frequently up to greater than 20:1, may include hydrocarbons of at least 6 carbon atoms and not more than about 30 carbon atoms, polyoxy compounds (alkyleneoxy compounds), where the oxygen atoms are joined by from about 2 to 10 carbon atoms, usually 2 to 6 carbon atoms, preferably 2 to 3 carbon atoms, and there will be at least about 6 units and usually not more than about 200 alkyleneoxy units, more usually not more than about 100 units, and preferably not more than about 60 units.

One Y is a bond to L, while the other Y is a monovalent oxy, thio, amino, sugar group or substituted functionalities thereof, or alkyl of up to about 20, usually of up to about 6 carbon atoms, when bonded to P, or hydrogen, hydrocarbyl or acyl of from 1 to 30, usually 1 to 12 carbon atoms, or substituted hydrocarbyl or acyl having from 1 to 4 hetero groups which are oxy, thio, or amino when bonded to Z.

a is at least 5 and not more than about 50, usually not more than about 35.

The phosphorus moiety may include phosphate, phosphoramidate, phosphordiamidate, phosphorothioate, phosphorothionate, phosphorothiolate, phosphoramidothiolate, phosphonate, phosphorimidate and the like.

The purines and pyrimidines may include thymidine, uracil, cytosine, 6-methyluracil, 4,6-dihydroxypyrimidine, isocytosine, hypoxanthine, xanthine, adenosine, guanosine, and the like.

The sugars may be ribose, arabinose, xylylose or α-deoxy derivatives thereof. Other nucleosides may also employ hexoses.

A wide variety of linking groups may be employed, depending upon the nature of the terminal nucleotide, the functionality selected for, whether the linking group is present during the synthesis of the oligonucleotide, the functionality present on the solubility modifying moiety and the like. A number of linking groups are commercially available and have found extensive use for linking polyfunctional compounds. The linking groups include: —OCH$_2$CH$_2$NHCO(CH$_2$)$_n$CONH—; —OCH$_2$CH$_2$NH—X—(CH$_2$)$_n$NH—; —O—P(O)(OH)NHCO(CH$_2$)$_n$CONH—; OCH$_2$CH$_2$NHCOφS—; —NH(CH$_2$)$_n$NH; —O(CH$_2$)$_n$O—; —O(CH$_2$CH$_2$NH)$_m$—; —NH(CH$_2$)$_n$SYN; —CO(CH$_2$)$_n$CO; —SCH$_2$CH$_2$CO—; —COφNYS—; —(NCH$_2$CH$_2$)$_m$CH$_2$N—; —O(CO)NH(CH$_2$)nNH; charged and uncharged homo- and copolymers of amino acids, such as polyglycine, polylysine, polymethionine, etc. usually of about 500 to 2,000 daltons; wherein X is 2,5-quinondiyl, Y is (3-succindioyl) to form succinimidyl, n is usually in the range of 2 to 20, more usually 2 to 12, and m is 1 to 10, usually 1 to 6.

The lipophilic/amphiphilic group may be a wide variety of groups, being aliphatic, aromatic, alicyclic, heterocyclic, or combinations thereof, usually of at least 6, more usually at least 12 and not more than about 500, usually not more than about 200 carbon atoms, having not more than about 1 heteroatom per 2 carbon atoms, being charged or uncharged, including alkyl of at least 6 carbon atoms and up to about 30 carbon atoms, usually not more than about 24 carbon atoms, fatty acids of at least about 6 carbon atoms, usually at least about 12 carbon atoms and up to about 24 carbon atoms, glycerides, where the fatty acids will generally range from about 12-24 carbon atoms, there being from 1-2 fatty acids, usually at the 2 or 3 positions or both, aromatic compounds having from 1 to 4 rings, either mono- or polycyclic, fused or unfused, polyalkyleneglycols where the alkylenes are of from 2-10, usually of from 2-6 carbon atoms, more usually 2-3 carbon atoms, there being usually at least about 6 units, more usually at least about 10 units, and usually fewer than about 500 units, more usually fewer than about 200 units, preferably fewer than about 100 units, where the alkylene glycols may be homopolymers or copolymers; alkylbenzoyl, where the alkyl group will be at least about 6 carbon atoms, usually at least about 10 carbon atoms, and not more than about 24 carbon atoms, usually not more than about 20 carbon atoms; alkyl phosphates or phosphonates, where the alkyl group will be at least about 6 carbon atoms, usually at least about 12 carbon atoms and not more than about 24 carbon atoms, usually not more than about 20 carbon atoms, or the like.

The solubility modifying group may be charged or uncharged, preferably being uncharged, under physiological conditions, usually having not more than 1 charge per 10 atoms of the group other than hydrogen. Illustrative groups include polyethylene glycol having from about 40-50 units, copolymers of ethylene and propylene glycol, laurate esters of polyethylene glycols, triphenylmethyl, naphthylphenylmethyl, palmitate, distearylglyceride, didodecylphosphatidyl, cholesteryl, arachidonyl, octadecanyloxy, tetradecylthio, etc.

Functionalities which may be present include oxy, thio, carbonyl (oxo or non-oxo), cyano, halo, nitro, aliphatic unsaturation, etc.

Of particular interest will be oligonucleotide conjugates of the following formula:

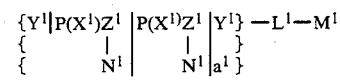

$X^1$ is nitrogen or oxygen;

$Z^1$ is ribose or deoxyribose substituted at the 3' and 5' positions;

One $Y^1$ is a bond to $L^1$ and the other $Y^1$ is hydroxy, alkyl, alkoxy or amino (including substituted amino, e.g., alkyl, acyl, etc.) of from 0 to 3 carbon atoms or a five carbon sugar, particularly ribose or deoxyribose, when bonded to P and hydrogen, alkyl, or acyl of from 1 to 10, usually 1 to 6 carbon atoms when bonded to $Z^1$;

$N^1$ is any purine or pyrimidine which can hybridize to the naturally occurring purines and pyrimidines, but is preferably a naturally occurring purine or pyrimidine;

$L^1$ is a linking group of at least about 2 carbon atoms and not more than about 30 carbon atoms, usually not more than about 20 carbon atoms, having from 0-10, usually 1-6 heteroatoms, which will be oxygen, nitrogen, and sulfur, particularly as oxy, amino, or thio;

$M^1$ is the solubility modifying moiety, hydrophobic or amphiphilic, which is desirably a polyalkyleneoxy group of at least about 20 units and not more than about 200 units, normally not more than about 150 units, where the alkylene groups are of from 2-3 carbon atoms;

$a^1$ is at least 5, usually at least 7 and generally not more than about 50, usually not more than about 30, more usually ranging from about 11 to 30, preferably from about 13 to 30.

In preparing the subject compositions, the oligonucleotide and the solubility modifying moiety will usually exist as independent moieties and may be joined together by a linker arm. The oligonucleotide may be made by any convenient synthetic procedure. For the most part, recombinant procedures will not be employed, although in some situations they may be useful. Various commercial synthetic devices for preparing polynucleotides are available from a number of companies, such as Applied Biosystems Inc., Biosearch, Inc. and Pharmacia. A variety of procedures are known for employing blocked oligonucleotides as their triesters, phosphoramidites, phosphonates, or the like, where a cycling procedure is employed, and the individual nucleotides are added in succession.

At the completion of the synthesis, various protocols may be employed. Preferably in most cases, the terminal blocking group may be removed and the linking arm joined to the terminal nucleotide. Alternatively, all of the blocking groups may be removed and the terminal nucleotide modified, by addition of the linking arm, where the linking arm may be specific for the final oligonucleotide. In some instances, the terminal blocking group may serve as all or part of the linking arm. Alternatively, the oligonucleotide may be removed from the support and then manipulated further, particularly where the linking group to the support may be used as the linking arm for joining the hydrophobic modifying moiety. Various procedures for further functionalization of the 5'- or 3'-termini of oligonucleotides may be found in Chu and Orgel *DNA* (1985) 4:327-331; Connolly and Rider *Nucl. Acids Res.* (1985) 13:4485-4502.

Depending upon the functionalities, various reactions may be employed to produce amides, esters, both inorganic and organic, oxygen and sulfur ethers, amines, or the like. In working with carboxyl groups, various activating groups may be employed, such as carbonyldiimidazole, carbodiimides, succinimidyl ester, paranitrophenyl ester, etc.

Various active functionalities can be employed, such as isocyanates, diazo groups, imino chlorides, imino esters, anhydrides, acyl halides, sulfinyl halides, isothiocyanates, sulfonyl chlorides, etc. Conditions for carrying out the various reactions in joining non-nucleotide moieties to nucleotide moieties may be found in Chu and Orgel *DNA* (1985) 4:327-331; Smith, et al. *Nucl. Acids. Res.* (1985) 13:2399-2412.

The solubility modifying moiety may be added to the linking arm either prior to, subsequent to or concurrently with the addition of the linking arm to the oligonucleotide. For the most part, the solubility modifying moiety will be added subsequent to the reaction of the linking arm to the oligonucleotide. In some instances, it may be desirable to join the solubility modifying moiety to the linking arm, where the linking arm is bound to the oligonucleotide while the oligonucleotide is still bound to the support. As already indicated, the reactions between the linking arm and the solubility modifying moiety will vary with the particular functional groups present, the nature of the hydrophobic moiety, reaction conditions which are required, and the like.

For the most part, reaction conditions will be mild, and will occur in polar solvents or combinations of polar and non-polar solvents. Solvents will vary and include water, acetonitrile, dimethylformamide, diethyl ether, methylene chloride, etc. Reaction temperatures will be for the most part in the range of about $-10°$ to $60°$ C. Usually, after completion of the reaction between components of the conjugate, the resulting product will be subjected to purification.

The manner of purification may vary, depending upon whether the oligonucleotide is bound to a support. For example, where the oligonucleotide is bound to a support, after addition of the linking arm to the oligonucleotide, unreacted chains may be degraded, so as to prevent their contaminating the resulting product. On such cases, the bonding of the linker to the oligonucleotide must be sufficiently stable to withstand the cleavage conditions from the synthesis support, e.g., conc. ammonia. Where the oligonucleotide is no longer bound to the support, whether only reacted with the linking arm or as the conjugate to the solubility modifying moiety intermediate or as the final product, each of the intermediates or final product may be purified by conventional techniques, such as electrophoresis, solvent extraction, HPLC, chromatography, or the like. The purified product is then ready for use.

The subject products will be selected to have an oligonucleotide sequence complementary to a sequence of interest. The sequence of interest may be present in a prokaryotic or eukaryotic cell, a virus, a normal or neoplastic cell. The sequences may be bacterial sequences, plasmid sequences, viral sequences, chromosomal sequences, mitochondrial sequences, plastid sequences, etc. The sequences may involve open reading frames for coding proteins, ribosomal RNA, snRNA, hnRNA, introns, untranslated 5'- and 3'-sequences flanking open reading frames, etc. The subject sequences may therefore be involved in inhibiting the availability of an RNA transcript, inhibiting expression of a particular protein, enhancing the expression of a particular protein by inhibiting the expression of a repressor, reducing proliferation of viruses or neoplastic cells, etc.

The subject conjugates may be used in vitro or in vivo for modifying the phenotype of cells, limiting the proliferation of pathogens such as viruses, bacteria, protists, mycoplasma, chlamydia, or the like, or inducing morbidity in neoplastic cells or specific classes of normal cells. Thus, one can use the subject compositions in therapy, by administering to a host subject to or in a diseased state, one or more of the subject compositions to inhibit the transcription and/or expression of the native genes of the cell. The subject compositions may be used for protection from a variety of pathogens in a mammalian host, e.g., enterotoxigenic bacteria, Pneumococcus, Neisseira, etc.; protists, such as Giardia, Entamoeba, etc.; neoplastic cells, such as carcinoma, sarcoma, lymphoma, etc.; specific B-cells, specific T-cells, such as helper cells, supressor cells, CTL, NK, ADCC, etc.

The subject sequences may be selected so as to be capable of interfering with transcription product maturation or expression of proteins by any of the mechanisms involved with the binding of the subject composition to its target sequence. These mechanisms may include interference with processing, inhibition of transport across the nuclear membrane, cleavage by endonucleases, or the like.

The subject sequences may be complementary to such sequences as sequences expressing growth factors, lymphokines, immunoglobulins, T-cell receptor sites, MHC antigens, DNA or RNA polymerases, antibiotic resistance, multiple drug resistance (mdr), genes involved with metabolic processes, in the formation of amino acids, nucleic acids, or the like, DHFR, etc. as well as introns or flanking sequences associated with the open reading frames.

The following table is illustrative of some additional applications of the subject compositions.

| THERAPEUTIC APPLICATIONS OF SYNTHETIC DNA TECHNOLOGY | |
|---|---|
| Area of Application | Specific Application Targets |
| Infectious Diseases: | |
| Antivirals, Human | AIDS, Herpes, CMV |
| Antivirals, Animal | Chicken Infectious Bronchitis |
| | Pig Transmissible Gastroenteritis Virus |
| Antibacterial, Human | Drug Resistance Plasmids, *E. coli* |
| Antiparasitic Agents | Malaria |
| | Sleeping Sickness (Trypanosomes) |
| Cancer | |
| Direct Anti-Tumor Agents | c-myc oncogene - leukemia other oncogenes |
| Adjunctive Therapy | Methotrexate Resistance - leukemia Drug Resistant Tumors - drug transport |
| Auto Immune Diseases | |
| T-cell receptors | Rheumatoid Arthritis Type I Diabetes Systemic Lupus Multiple sclerosis |
| Organ Transplants | Kidney - OTK3 cells cause GVHD |

The subject compositions may be administered to a host in a wide variety of ways, depending upon whether the compositions are used in vitro or in vivo. In vitro, the compositions may be introduced into the nutrient medium, so as to modulate expression of a particular gene by transfer across the membrane into the cell interior such as the cytoplasm and nucleus. The subject compositions can find particular use in protecting mammalian cells in culture from mycoplasma, for modifying phenotype for research purposes, for evaluating the effect of variation of expression on various metabolic processes, e.g., production of particular products, variation in product distribution, or the like. While no particular additives are necessary for transport of the subject compositions intracellularly, the subject compositions may be modified by being encapsulated in liposomes or other vesicles, and may be used in conjunction with permeabilizing agents, e.g., non-ionic detergents, Sendai virus, etc.

For in vivo administration, depending upon its particular purpose, the subject compositions may be administered in a variety of ways, such as injection, infusion, tablet, etc., so that the compositions may be taken orally, intravascularly, intraperitoneally, subcutaneously, intralesionally, or the like. The compositions may be formulated in a variety of ways, being dispersed in various physiologically acceptable media, such as deionized water, water, phosphate buffered saline, ethanol, aqueous ethanol, or formulated in the lumen of vesicles, such as liposomes or albumin microspheres.

Because of a wide variety of applications and manners of administration, no particular composition can be suggested. Rather, as to each indication, the subject compositions may be tested in conventional ways and the appropriate concentrations determined empirically. Other additives may be included, such as stabilizers, buffers, additional drugs, detergents, excipients, etc. These additives are conventional, and would generally be present in less than about 5 wt %, usually less than 1 wt %, being present in an effective dosage, as appropriate. For fillers, these may be as high as 99.9% or greater of the composition, depending upon the amount of active material necessary.

The following examples are presented by way of illustration not by way of limitation.

EXPERIMENTAL

EXAMPLE 1

Synthesis of Polyethylene Glycol Derivatives of Normal DNAs Using Aminolink, Benzoquinone and Bis-(Aminohexyl) Polyethylene Glycol Chemical Synthesis of DNA oligonucleotides by the Amidite Method The chemical synthesis of DNA can be carried out using slight modifications of the conventional phosphoramidite methods on any commercially available DNA synthesizer. This method is a modification of the technique described by Caruthers and coworkers (Beaucage and Caruthers, Eur. patent application 82/102570.

In this technique, 0.1 M nucleoside phosphoramidites dissolved in anhydrous acetonitrile were mixed with an equal volume of 0.5 M tetrazole and sequentially coupled to the 5'-hydroxyl terminal nucleotide of the growing DNA chain bound to controlled pore glass supports via a succinate spacer (Matteucci and Caruthers, *Tetrahedron Letters* (1980) 21:719–22. Nucleoside addition was followed by capping of unreacted 5'-hydroxyls with acetic anhydride, iodine oxidation, and 5'-detritylation in trichloroacetic acidmethylene chloride. The resin-bound oligomer was then dried by extensive washing in anhydrous acetonitrile and the process repeated. Normal cycle times using this procedure were 12 minutes with condensation efficiencies of >98% (as judged by trityl release).

As the last step of the synthesis, trityl was removed from the product oligonucleotide chains and an aminoethanolphosphoramidite was added to the 5'-hydroxyl using Aminolink (Applied Biosystems, Foster City, CA). The resin-bound oligonucleotide was then deblocked and released from the column using a method appropriate to the type of phosphate linkage present. For normal phosphodiesters, release from the column and hydrolysis overnight at 55° C. in concentrated ammonium hydroxide was appropriate.

The product was then lyophilized several times from 50% aqueous ethanol and purified via reversed phase HPLC C-8 silica columns, eluting with 5 to 50% acetonitrile/25 mM ammonium acetate, pH 6.8 in a linear gradient. If required, the material may be further purified by ion-exchange HPLC on Nucleogen DEAE 60-7 eluting with 20% acetonitrile/25 mM ammonium acetate, pH 6.5. The recovered product was then characterized by gel electrophoresis on 15% polyacrylamide gels carried out as described by Maxam and Gilbert in *Methods of Enzymology* (1980) 68:499–560. Oligonucleotides in finished gels were visualized using Stains-all. The Stains-All procedure did not work for uncharged oligonucleotides such as DNA methylphosphates or ethyl triesters.

The fully deblocked and purified product is then converted to the appropriate polyethylene glycol derivative using a suitable coupling technique. Several techniques can be used including benzoquinone, carbodiimide, SMCC (Succinimidyl 4-(N-maleimideomethyl)-cyclohexane-1-carboxylate, SPDP (N-succinimidyl 3-(2-pyridyldithio)propionate, carbonyldiimidazole, Aminolink, disuccinimidyl suberimidate and phenylisocyanate.

Coupling of the Linker Arm DNA to Benzoquinone and Cross-Linking to Bis(aminohexyl) Polyethylene Glycol In the first step bis-(aminohexyl)polyethylene glycol is reacted with a 100 to 1000 fold molar excess of benzoquinone in 0.1 M sodium bicarbonate (pH 8.5). After 1 hour at room temperature, the excess unreacted benzoquinone is removed by Sephadex G-25 column chromatography. The activated polyethylene glycol is then made to 0.1 M sodium bicarbonate and reacted with the DNA oligomer containing a reactive amine linker arm in a molar ratio of 10:1 and the reaction allowed to proceed to completion. At the end of the reaction (generally overnight) the unreacted oligomer is removed by gel-filtration on Sephadex G-100 and the complex characterized by polyacrylamide gel electrophoresis (cf. Maniatis, et al., Molecular cloning, A laboratory manual (1982) Cold Spring Harbor Laboratories, Cold Spring Harbor, NY). Further purification can be effected using ion-exchange chromatography and gel electrophoresis as required.

The structure of the product of these reactions is:

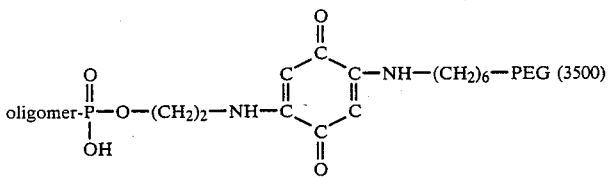

EXAMPLE 2

Synthesis of Polyethylene Glycol Derivatives of Normal DNAs Using Aminolink and Carbonyldiimidazole Activated Polyethylene Glycol In this example the Aminolink oligonucleotide was synthesized as described in Example I. After removal of the oligomer from the support and deblocking in ammonia, the solution was evaporated in vacuo and dissolved in 0.1 M NaHCO3, pH 8.5 and purified on a G25-spun column to convert the material to the sodium salt and to remove any extraneous amine-containing material of low molecular weight. The solution was then made to 0.2 M in carbonyldiimidazole-activated polyethylene glycol (MW$_{av}$=20,000) and allowed to react overnight at 23° C.

Unbound oligonucleotide was removed by gel filtration on Sephadex G-100. On this column the complex elated in the excluded volume of the column while the free oligonucleotide and unbound polyethylene glycol were retained. This material was then concentrated in vacuo and the complex characterized by polyacrylamide gel electrophoresis (Maniatis et al., (1982), supra.

EXAMPLE 3

Synthesis of Polyethylene Glycol Derivatives of Normal DNAs Using Phosphoramidate Linker Amines and N-Hydroxysuccinimidyl Activated Polyethylene Glycol In this method DNA is synthesized as in Example 1 with the exception that the trityl group is removed without the further addition of the Aminolink phosphoramidite. After purification by polyacrylamide gel electrophoresis, the product DNA is phosphorylated with the forward reaction of T4 polynucleotides kinase according to standard procedures (Miller et al., *Nucl. Acids. Res.* (1983) 11:6225–42; Maniatis et al., (1982), supra; Maxam and Gilbert, *Proc. Nat'l Acad. Sci. USA* (1980) 74:560–5. Labeled oligomers can be separated from unreacted ATP by DEAE chromatography and C-18 reverse phase columns (e.g. Waters C-18 SepPak). Samples are checked for purity on analytical 20% polyacrylamide gels.

The phosphorylated oligomer is then treated with 1-methylimidazole and hexanediamine, in the presence of EDC carbodiimide according to the method of Chu and Orgel DNA (1985) 4:327–31. This reaction covalently couples the diamine linker to the oligonucleotides via a phosphoramidate linkage with the following structure:

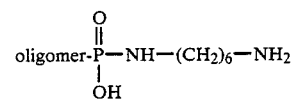

The amine linker arm oligomer is then conjugated to NHS-succinylmonomethoxypolyethylene glycol (MW 5000) as follows. The oligonucleotide is dissolved to a final concentration of 100 μM per liter in 50 mM sodium phosphate buffer, pH 7.1 containing 0.15 M NaCl. To this solution a 10 fold molar excess of SSPEG (5000) is added as a dry solid, allowed to dissolve and the reaction mixture incubated overnight at 25° C. The product is then purified by gel filtration chromatography on Sephadex G-100 in water and characterized by polyacrylamide gel electrophoresis.

The structure of the final product is:

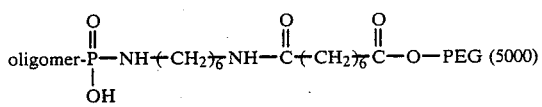

EXAMPLE 4

Synthesis of Polyethylene Glycol Derivatives of Normal DNAs Using Imidazole Activated Carboxylic Acid Esters and Bis-Aminoalkyl Polyethylene Glycol In this example, DNA was synthesized according to the method given in Example 1. After synthesis, the product material was retained on the synthesis support with trityl removed from the 5' end of the molecule. The solid material was then thoroughly washed with anhydrous acetonitrile and blown dry under a stream of dry argon. Using a plastic syringe, 1 cc of 0.3 M carbonyldiimidazole dissolved in anhydrous acetonitrile was pushed slowly through the synthesis column containing the support bound oligomer over the course of 1 hour. The 5' carbonylimidazole activated oligomer on the column was then washed free of excess reagent with 15 ml of acetonitrile and subsequently treated for 16 hours with 0.1 M bis (aminohexyl) polyethylene glycol in acetonitrile, water, acetonitrile and methylene chloride in succession. The polyethylene oligomer conjugate was then eluted with concentrated ammonium hydroxide and deblocked in the same by incubation at 55° C. for 5 hours.

The reaction product is then purified by high performance gel filtration chromatography (HPGFC) on a TSK G4000SW column eluting 10 mM Tris, pH 7.5 at 0.5 ml per minute. Further purification may be effected by agarose gel electrophoresis. The structure of the final conjugate synthesized by this method is:

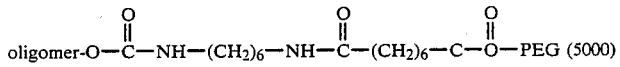

EXAMPLE 5

Synthesis of Long Chain Alkane Derivatives of Normal DNAs Using Imidazole Activated Carboxylic Acid Esters and Aminoalkanes In this example, a 20 nucleotide DNA complementary to the initiation region of mouse $\beta$-globin mRNA was synthesized according to the method given in Example 1. After synthesis, the product material was retained on the synthesis support with trityl removed from the 5' end of the molecule. The solid material was then thoroughly washed with anhydrous acetonitrile and blown dry under a stream of dry argon. Using a plastic syringe, 1 cc of 0.3 M carbonyldiimidazole dissolved in anhydrous acetonitrile was pushed slowly through the synthesis column containing the support-bound oligomer for 45 minutes. The 5' carbonylimidazole activated oligomer on the column was then washed free of excess reagent with 15 ml of acetonitrile and then treated with 0.2 M decanediamine in acetonitrile: water (10:1) for 30 minutes.

The material on the column was washed free of unreacted decanediamine with acetonitrile and water and then eluted from the column in concentrated ammonium hydroxide solution. After removal from the column, the ammonium hydroxide solution containing the oligomer conjugate was placed in a sealed vial and incubated 5 hours at 55° C.

The product was then lyophilized several times from 50% aqueous ethanol and purified via reversed phase HPLC C-8 silica columns eluted with 5 to 50% acetonitrile/25 mM ammonium acetate, pH 6.8 in a linear gradient. If required, the material may be further purified by ion-exchange HPLC on Nucleogen DEAE 60-7 using 20% acetonitrile/25 mM ammonium acetate, pH 6.5 as eluent. The recovered product was then characterized by gel electrophoresis in 15% polyacrylamide gels carried out as described by Maxam and Gilbert in *Meth. Enzymol.* (1980) 68:499–560. Oligonucleotides in finished gels were visualized using Stains-all.

The presence of a primary amine was determined by two methods. First, reaction with fluorescamine produced a fluorescent product characteristic of the presence of a primary amine while no fluorescence was observed with similarly treated control oligomers of the same type but lacking the amine linker. Second, the decane conjugate was dissolved in 100 μl 0.1 M sodium bicarbonate to which was added 1 mg of fluoresceinisothiocyanate (FITC). After 1 hour of incubation, the unreacted FITC was removed by gel filtration chromatography on Sephadex G-25 spun columns. The product was then analysed by polyacrylamide gel electrophoresis as described above and the fluorescent band product visualized under UV illumination. A single fluorescent band was observed which corresponded to the oligomer visualized by subsequent staining with Stains-all.

The product of this reaction is an alkyl carbamate which is stable to moderate exposure to concentrated base. The structure of the final conjugate synthesized by this method is:

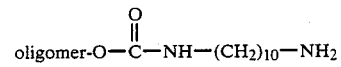

Other monoaminoalkyl and aryl derivatives can be produced by this method. Other molecules in this series which have been constructed include the derivatives made with ethylene diamine and hexane diamine. Higher chain length additions may require slight modifications of the solvent polarity in order to achieve the necessary concentrations. Alternatively, lower concentrations may be used if the reaction times are extended.

EXAMPLE 6

Synthesis of Polyethylene Glycol Derivatives of DNAs Using Imidazole-Activated Carboxylic Acid Esters, Polylysine Linker, DSS AND BIS-Aminoalkyl Polyethylene Glycol In this example, a 25 nucleotide DNA complementary to the initiation region of mouse $\beta$-globin mRNA was synthesized according to the method given in Example 1. After synthesis, the synthesis support was treated with 80% acetic acid for 30 minutes to remove trityl from the 5' end of the molecule. The solid material was then thoroughly washed with anhydrous acetonitrile and blown dry under a stream of dry argon and treated with 0.3 M carbonyldiimidazole as in Example 4. The 5' carbonyldiimidazole-activated oligomer on the column was then washed free of excess reagent with 15 ml of acetonitrile and then treated with 0.2 M poly-L-lysine (MW=1000) dissolved in 50% acetonitrile containing 0.1 M sodium phosphate, pH 8 for 16 hours at room temperature.

The material on the column was washed free of salts and unreacted polylysine with water and acetonitrile and then eluted from the column with concentrated ammonium hydroxide. After removal from the column, the ammonium hydroxide solution containing the oligomer conjugate was incubated 5 hours at 55° C. in a sealed glass vial. The product was then lyophilized several times from 50% aqueous ethanol and purified via gel filtration chromatography on TSK G4000SW in 10 mM Tris buffer, pH 7.5. The presence of a primary amine was determined by reaction with fluorescamine. No fluorescence was observed with control oligomers lacking the polyamine linker.

In order to render the polyamine conjugate negatively charged, the complex was reacted with FITC to label the molecule and to neutralize the positive charges on the amines. This was accomplished by dissolving a portion of the material in 100 μl 0.1 M sodium bicarbonate to which was added 1 mg of FITC. After 1 hour of incubation, the unreacted FITC was removed by gel filtration chromatography on Sephadex G-25 spun columns (Maniatis et al., (1982), supra. The product was then analysed by polyacrylamide gel electrophoresis carred out as described by Maxam and Gilbert (1980) supra and the fluorescent band product visualized under UV illumination. A broad fluorescent band was observed which corresponds to the DNA visualized by Stains-all.

The oligomer containing polylysine covalently linked to the 5' end of the molecule was then cross-linked to bis-(aminohexyl) polyethylene glycol (MW=3500) as follows. The polylysine oligomer is first dialysed against 0.1 M sodium carbonate, 3 M NaCl and concentrated to a final concentration of 4 mg/ml using a Centricon 10 apparatus (Amicon, Danvers, NJ). To 50 μl of this solution was added 25 μl of disuccinimidyl suberate (DSS, 10 mg/ml in DMSO) and the mixture incubated 10 minutes at room temperature. The unreacted DSS was then quickly removed by gel filtration on Sephadex G25 and concentrated on Centricon 10 membranes. The solution was then made to 0.2 M in bis-(aminohexyl) polyethylene glycol and incubated overnight at room temperature to form the final conjugate. Purification was effected on TSK G4000 SW columns operated as previously described.

This conjugate has the following general formula:

1. Formulation Type I

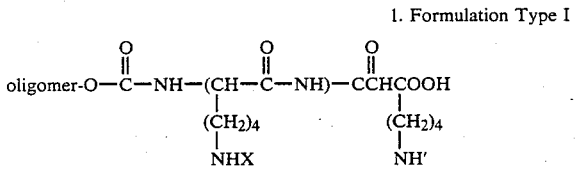

Where X is usually H, at least one X being —CO(CH$_2$)$_6$COHN—PEG$_{5000}$.

By varying the reaction excess or the molecular weight of the polyethylene glycol and the polylysine used it is possible to construct polymer conjugates with varying degrees of substitution size and charge. The ability to vary these properties of the complex make it possible to design the use of the compound in various applications.

EXAMPLE 7

Synthesis of Polyethylene Glycol Derivatives of DNA Methylphosphonates

The chemical synthesis of DNA methylphosphonates (MP) may be carried out using a modification of the phosphochloridite method of Letsinger (Letsinger et al., *J. Amer. Chem. Soc.* (1975) 97:3278; Letsinger and Lunsford, *J. Amer. Chem. Soc.* (1976) 98:3605–3661; Tanaka and Letsinger, *Nucl. Acids. Res.* (1982) 25:3249–60. In this procedure, dried blocked nucleosides dissolved in anhydrous acetonitrile 2,6-lutidine, are activated in situ with a stoichiometric amount of methyl dichlorophosphine. The activated nucleoside monochloridites are then added sequentially to the 5' hydroxy terminal nucleotide of the growing DNA chain bound to controlled pore glass supports via a succinate spacer (Matteucci and Caruthers, *Tetrahed. Lett.* (1980) 21:719–722. Each addition is followed by capping of unreacted 5'-hydroxyls with acetic anhydride, iodine oxidation, and 5'-detritylation in 3% trichloroacetic acid-methylene chloride.

The resin-bound methylphosphonate oligomers are then dried by extensive washing in anhydrous acetonitrile and the process repeated. Normal cycle times using this procedure are 23 minutes with condensation efficiencies of >32% (as judged by trityl release). The ultimate base may be added as the cyanoethyl phosphotriester which yields, upon cleavage in base, a 5'-terminal phosphodiester. This step makes it possible to radiolabel the oligonucleotide, purify and sequence the product using gel electrophoresis at intermediate stages of preparation (Narang et al., *Can. J. Biochem.* (1975) 53:392–394. Miller et al., *Nucl. Acids Res.* (1983) 11:6225–6242.

An amine-terminated linker arm is then added as follows. Trityl is removed as before and the resin treated with 0.2 M Aminolink (Applied Biosystems, Foster City, CA) dissolved in dry acetonitrile containing 0.2 M dimethylaminopyridine for 5 minutes. The linker arm oligonucleotide is then oxidized in iodine and washed in acetonitrile as above. Capping with acetic anhydride is not performed since any deblocked primary amine would be modified to the base-stable acetamide and thus be unavailable for further reaction.

At the end of the synthesis, the amine terminated linker arm methylphosphonate oligomer is base deblocked as follows. The resin containing the DNA is removed from the column and placed in a water jacketed column and incubated in 1–2 ml phenol:ethylene diamine (4:1) for 10 hours at 40° C. At the end of the incubation in phenol:ethylene diamine, the resin is washed free of the phenol reagent and base protecting groups released using methanol, water, methanol and methylene chloride in succession. After drying in a stream of nitrogen, the intact, base-deblocked chains are cleaved from the support using EDA:ethanol (1:1) or a brief treatment at room temperature with ammonium hydroxide.

Purification of the amine-terminated DNA methylphosphonate is then performed as follows. The material is first lyophilized several times from 50% aqueous ethanol and purified via reversed phase HPLC C-8 silica columns eluted with 5 to 50% acetonitrile/25 mM ammonium acetate, pH 6.8 in a linear gradient. Amine-containing fractions, as determined by fluorescamine reactivity, are pooled and the product recovered by drying in vacuo and further purified by ion-exchange HPLC on Nucleogen DEAE 60-7 eluted with 20% acetonitrile/25 mM ammonium acetate, pH 6.5.

The purified product is then converted to the appropriate polyethylene glycol derivative using the heterobifunctional crosslinking agents SMCC and SATA (succinimidyl S-acetylthioacetate). Reactions using other reagents which can react with and modify the nucleoside bases (e.g. sulfonyl chlorides, glutaraldehyde or acid anydrides) are not recomended unless performed with the fully blocked oligonucleotide still bound to the synthesis support.

The DNA methylphosphonate containing 5' terminal reactive amine linker arms is first reacted with SATA in a 100–1000 fold molar excess at pH 8.5 (0.1 M sodium bicarbonate). After 30 minutes at room temperature, the excess unreacted SATA is removed by G-25 column chromatography in water, concentrated in vacuo and stored cold until ready for further reaction. Bis-(aminohexyl) polyethylene glycol is converted to the maleimide derivative by treatment with a 100–1000 fold molar excess of SMCC in 0.1 M phosphate buffer, pH 6.9 for 1 hour at room temperature. Excess crosslinking agent is removed by chromatography on Sephadex G-100 and the material concentrated in vacuo and stored cold until ready for further reaction. This material is stable for about one week when kept cold. The SATA DNA methylphosphonate is then treated with hydroxylamine HCl dissolved in 0.1 M phosphate buffer (pH adjusted to 7.2) for 1–2 hours. This treatment serves to release the reactive sulfhydryl. This product is then reacted overnight with a 10 fold molar excess of bis-(SMCC aminohexyl) polyethylene glycol by addition of the latter as a powder to the solution containing the oligomer.

Purification of the complex is then effected. Unbound oligonucleotide is removed by gel filtration on Sephadex G-100 or HPGFC on TSK G400SW eluted with 10 mM Tris, pH 7.5. The diagrammatic structure of the final product of this procedure is:

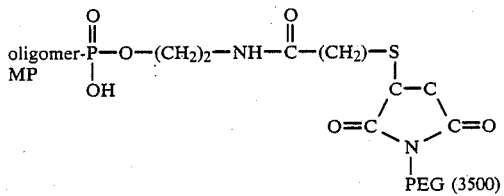

EXAMPLE 8

Synthesis of Polyethylene Glycol Derivatives of DNA Alkyltriesters Using the Phosphoramidite Approach The synthesis of the title compound triesters is performed according to the method of Zon and coworkers (Gallo et al., *Nucl. Acids. Res.* (1986) 14:7405-20; Summers et al., *Nucl. Acids Res.* (1986) 14:7421-36. The method of synthesis is similar to that used for in situ production of ethyl triesters as described in the other examples. Fully blocked dimethoxytrityl nucleosides are dried by repeated lyophilization from benzene, dissolved in anhydrous acetonitrile/2,6-lutidine and added dropwise to a stirred solution of chlorodiisopropylaminoethoxyphosphine in the same solvent at −70° C. The product is recovered by aqueous extraction, drying in vacuo and silica gel chromatography.

The chemical synthesis of DNA ethyl triesters (ETE) can be carried out using slight modifications of the conventional phosphoramidite methods. In this technique, nucleoside phosphoramidites dissolved in anhydrous acetonitrile are mixed with tetrazole and sequentially coupled to the 5'-hydroxy terminal nucleoside bound to CPG. Nucleoside addition is followed by capping of unreacted 5'-hydroxyl with acetic anhydride, iodine oxidation, and 5'-detritylation in trichloroacetic acid-methylene chloride. The resin-bound oligomer is then dried by extensive washing in anhydrous acetonitrile and the process repeated. Normal cycle times using this procedure are 17 minutes with condensation efficiencies of >96% (as judged by trityl release). The terminal residue is conventionally added as a diester in order to facilitate radiolabeling and purification. The 5'-terminal trityl group is left if HPLC purification is desired, but generally the 5'-terminal trityl is removed and the Aminolink procedure described in Example 1 is used.

At the end of the synthesis, the fully blocked product is base-deblocked as follows. The resin containing the fully protected DNA is removed from the column and placed in a water-jacketed chromatography column. The resin is then incubated in 1–2 ml phenol: ethylene diamine (4:1) for 10 hours at 40° C. At the end of the incubation in phenol:ethylene diamine, the resin is washed free of the phenol reagent and base protecting groups released using methanol, water, methanol and methylene chloride in succession. After drying in a stream of nitrogen, the intact, base-deblocked chains are cleaved from the support using EDA:ethanol (1:1) or a brief treatment at room temperature with ammonium hydroxide.

Purification of the Aminolink DNA ethyl triester product is then performed as follows. The material is first lyophilized several times from 50% aqueous ethanol and purified via reversed phase HPLC C-8 silica columns eluted with 5 to 50% acetonitrile/25 mM sodium acetate, pH 6.8 in a linear gradient. Amine-containing fractions as determined by fluorescamine reactivity are pooled and the product recovered by drying in vacuo and further purified by ion-exchange HPLC on Nucleogen DEAE 60-7 eluting 25% acetonitrile/25 mM ammonium acetate, pH 6.5.

The product oligonucleotide is then suitable for coupling to polyethylene glycol by any of the techniques previously described. In our experiments several techniques have been used, including SMCC, SPDP, carbonyldiimidazole, disuccinimidyl suberimidate and phenylisocyanate.

The SMCC/SPDP coupling reaction is as follows. The linker arm probe is coupled to excess SPDP followed by reduction with dithiothreitol (DTT), the unreacted DTT removed and the product allowed to cross-link through the free sulfhydryl to SMCC previously coupled to bis-(aminohexyl) polyethylene glycol (PEG). The formation of the thioether linkage is rapid and selective and the linkage formed is quite stable to a variety of conditions. The precise method of linkage formation is as follows:

The DNA containing amine linker arms is reacted with SPDP in a 100–1000 fold molar excess at pH 8.5

(0.1 M sodium bicarbonate). After 1 hour at room temperature, the excess unreacted reagent is removed by G-25 column chromatography and the probe SPDP conjugate concentrated in vacuo. Bis-(aminohexyl) polyethylene glycol is converted to the maleimide derivative as described in the previous example. The SPDP DNA triester is then treated with 10 mM mercaptoethanol dissolved in 0.1 M phosphate buffer (pH adjusted to 7.2) for 1 hour. This treatment serves to release the 5′ thiopyridone thus forming a reactive sulfhydryl. Excess reducing agent is then removed using a G-25 spun column operated as previously described with the exception that all separations are performed in degassed 0.1 M phosphate buffer, pH 6.8 under a nitrogen atmosphere to prevent the reoxidation of the terminal SH. In this procedure it is essential that all excess reducing agent be removed in order to prevent its subsequent reaction with the maleimidylated polyethylene glycol.

Thiopyridone released in this procedure provides a convenient indirect method for quantitating the presence of the 5′-terminal SH. Thiopyridone released by reduction has a UV absorption at 343 nm. By following the increase in absorbance of the solution at this wavelength, the course of the reduction is easily followed. The thiopyridone can then be quantitated using a molar extinction coefficient of 8080. The product is then reacted overnight with a 10 fold molar excess of bis-(SMCC-aminohexyl) polyethylene glycol by addition of the latter as a powder or a concentrated solution to the solution containing the SH terminated oligomer triester. The reaction is allowed to proceed overnight at 25° C.

Purification of the complex is then effected. Unbound oligonucleotide is removed by gel filtration on Sephadex G-100 or HPGFC on TSK G4000SW eluted with 10 mM Tris, pH 7.5. The diagrammatic structure of the final product of this procedure is:

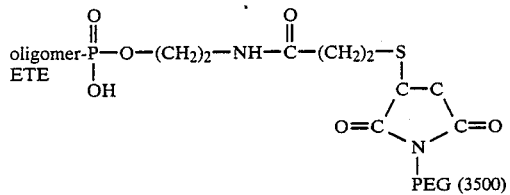

EXAMPLE 9

Synthesis of Polyether Derivatives of DNA Alkyl and Aryltriesters Using the Phosphate Triester Approach Synthesis of Phosphotriester Oligonucleotides of Varying Alkyl and Aryl Substituent Type The best available method for the production of the various triesters of variable alkane chain length is via conventional phosphate triester chemistry to synthesize the desired sequences as the b-chlorophenyl phosphate triesters (PTE). Upon completion of the synthesis, the fully protected oligonucleotide chlorophenyltriesters bound to the synthesis support are subjected to ester exchange in the presence of tetrabutylammonium fluoride and the desired alcohol. This basic method for the construction of DNA oligonucleotides is classical DNA synthesis chemistry. See Gait, (1984) *Olignucleotide Synthesis: A Practical Approach*, IRL Press, Washington, DC.

The chemical synthesis of DNA p- or o-chlorophenyl phosphotriesters was carried out using a modification of the phosphochloridite method of Letsinger Tanaka and Letsinger, *Nucl. Acids Res.* (1982) 25:3249–60. For automated DNA synthesis, see Alvarado-Urbina et al., *Science* (1981) 214:270–273.

Fully blocked and dried nucleosides dissolved in anhydrous acetonitrile 2,6-lutidine and activated in situ with chlorophenoxydichlorophosphine are sequentially added to the 5′-hydroxy terminal nucleotide of the growing DNA chain bound to controlled pore glass supports via a succinate spacer as in previous examples. Derivatized glass supports, fully blocked nucleosides and other synthesis reagents are commercially available through Applied Biosystems (San Francisco, CA) or American Bionuclear (Emeryville, CA). Nucleoside addition is followed by capping of unreacted 5′-hydroxyls with acetic anhydride, iodine oxidation, and 5′-detritylation in trichloroacetic acid-methylene chloride.

The resin bound oligomer chlorophenyltriester is then dried by extensive washing in anhydrous acetonitrile and the process repeated. Normal cycle times using this procedure are 13 minutes with condensation efficiencies of >92% (as judged by trityl release). The ultimate base may be added as a β-cyanoethyl phosphotriester which yields, upon cleavage in base, a 5′-terminal phosphodiester. This step makes it possible to radiolabel the oligonucleotide and to purify and sequence the product using gel electrophoresis (Narang et al., *Can. J. Biochem.* (1975) 53:392–4; Miller et al., *Biochemistry* (1986) 25:5092–97.

The fully blocked material bound to the synthesis support is then subject to ester exchange in the presence of tetrabutylammonium fluoride (TBAF) and the desired alcohol under anhydrous conditions. This method yields rapid and quantitative alcohol exchange. The reaction is complete within 20 minutes for most aryl and alkyl alcohols which are capable of forming stable products.

In this example, anhydrous n-propanol is used to dissolve TBAF to a final concentration of 0.2 M. The solution is then percolated slowly over the resin containing the oligomer chlorophenyl triester and allowed to react for about 1 hour at room temperature. The resin is then washed with methanol and acetonitrile and dried under a stream of dry argon. Amine linker arm addition, deblocking and purification are then effected as in Example 8. Polyethylene glycol conjugation is performed as in Example 7. The final yield of conjugate is about 10% of the starting equivalents of nucleoside resin used. The diagrammatic structure of the final product is:

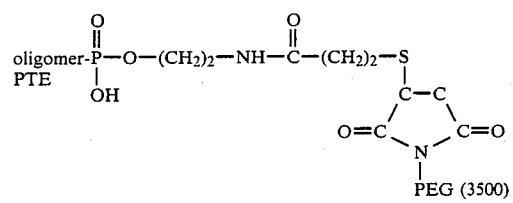

EXAMPLE 10

The Effect of Trityl Terminated Oligonucleotides on the Synthesis of β-globin Protein in vitro and in Cultured Cells Using the methods of synthesis provided in the previous examples, both normal and ethyl triester type oligonucleotides were constructed. In the simplest example of an amphiphilic DNA conjugate containing a hydrophobic grouping at the 5' end of the molecule, the trityl group is left on at the end of the synthesis. Purified materials of this type were tested for their effectiveness in preventing the specific expression of hemoglobin in mouse erythroleukemia cells induced to produce hemoglobin. The oligonucleotides tested in these and the following examples are given in Table I.

The cells chosen for these experiments are Friend murine erythroleukemia (MEL) cells which can be induced to synthesize hemoglobin by a variety of agents including DMSO and butyric acid (cf. Gusella and Houseman, Cell (1976) 8:263–269. MEL cells are grown in culture using conventional techniques in a $CO_2$ incubator.

Induced cells which are expressing globin can be visualized by benzidine treatment which stains hemoglobin-producing cells blue (Leder et al., Science (1975) 190:893. Cells were exposed to the selected oligonucleotide conjugates at concentrations ranging from 1 mg/ml to 1 μg/ml during induction. Controls included mock-treated cells and cells treated with random sequence oligomer controls. Treated cells were scored at various time intervals for globin production based on staining intensity and the results compared to controls. About 50% of the control cells are inducible. Cell death or damage due to treatment is scored by Trypan blue exclusion in order to obtain an indication of toxicity and cell damage.

The results obtained are presented in Table II. These results show that the trityl terminated oligomers are more effective in producing the desired degree of synthesis inhibition. The trityl modified oligomers however showed some degree of cell damage which would not recommend their general use as therapeutic agents.

TABLE II
EFFECT OF TRITYLATED OLIGOMERS ON HEMOGLOBIN ACCUMULATION IN MOUSE CELLS

| Oligmer Conjugate* | Viable Cells (% of Control) | % Benzidine* (B*) | % Inhibition B* Cells |
|---|---|---|---|
| DMSO Control | 100% | 100% | 0% |
| MBG 15 100 μM | 100% | 68% | 32% |
| MBG 15 ETE 50 μM | 95% | 59% | 41% |
| MBG 15 ETE-DMT 50 μM | 94% | 43% | 57% |

*See Table I. ETE is ethyl triester.

TABLE I
DNA SEQUENCES SYNTHESIZED AND CONJUGATED FOR USE IN CELL CULTURE EXPERIMENTS

| Probes Synthesized Antisense to Mouse Beta-globin mRNA | % GC | Sequence (3' to 5') |
|---|---|---|
| MBG 15 antisense | 60% | G TAC CAC GTG GAC TG |
| MBG 15 antisense-DMT | 60% | G TAC CAC GTG GAC TG—DMT |
| MBG 15 antisense-$C_2$ amine | 60% | G TAC CAC GTG GAC TGp—O—$(CH_2)_2$—$NH_2$ |
| MBG 15 ethyl triester | 60% | g tac cac gtg gac tG |
| MBG 15 ethyl triester-DMT | 60% | g tac cac gtg gac tG—DMT |
| MBG 20 antisense | 55% | G TAC CAC GTG GAC TGA CTA C |
| MBG 20 antisense $C_2$ | 55% | G TAC CAC GTG GAC TGA CTA Cp—O—$(CH_2)_2$—$NH_2$ |
| MBG 20 antisense $C_6$ | 55% | G TAC CAC GTG GAC TGA CTA C—O—(C))—NH—$(CH_2)_6$—$NH_2$ |
| MBG 20 antisense $C_{10}$ | 55% | G TAC CAC GTG GAC TGA CTA C—O—(CO)—NH—$(CH_2)_{10}$—$NH_{62}$ |
| MBG 20 antisense $C_2$—FITC | 55% | G TAC CAC GTG GAC TGA CTA Cp—O—$(CH_2)_2$—$NH_2$—FITC |
| MBG 20 antisense $C_6$—FITC | 55% | G TAC CAC GTG GAC TGA CTA C—O—(CO)—NH—$(CH_2)_6$—NH—FITC |
| MBG 20 antisense $C_{10}$—FITC | 55% | G TAC CAC GTG GAC TGA CTA C—O—(CO)—NH—$(CH_2)_{10}$—NH—FITC |
| MBG 20 antisense $C_2$—PEG | 55% | G TAC CAC GTG GAC TGA CTA Cp—O—$(CH_2)_2$—$NH_2$—PEG |

(a) Lower case letters represent nucleosides coupled to the 3' adjacent nucleoside via an ethyl phosphotriester linkage. Upper case letters represent 3' adjacent normal phosphodiester linkage. DMT represents a 5' terminal dimethoxytrityl moiety. $C_2$ derivatives are formed from the condensation of ethanolamine with a 5' terminal phosphate via an ester linkage. $C_6$ and $C_{10}$ derivatives are the corresponding diamines coupled via an alkyl carbamate linkage to the 5' terminal hydroxyl. FITC represents the condensation product of fluoresceinisothiocyanate (isomer I) with the indicated diamine. PEG is polyethylene glycol ($M_r = 3500$).

EXAMPLE 11

The Effect of Long Chain Alkyl Terminated Oligonucleotides on the Synthesis of β-globin Protein in Cultured Cells Using the method of synthesis provided in the previous examples, 15 to 20 base long oligonucleotides conjugated to a 5'-terminal aminoalkane were constructed as described in Example 5. Purified materials of this type were tested for their effectiveness in preventing the specific expression of hemoglobin in MEL cells induced to produce hemoglobin. The results are given in Table III. The protocol for the test is given in Example 10.

TABLE III

THE EFFECT OF INCREASING HYDROPHOBICITY ON THE EFFECTIVENESS OF OLIGONUCLEOTIDES IN PREVENTING HEMOGLOBIN SYNTHESIS IN CULTURED CELLS

| Treatment | Viable Cells | Inhibition of Benzidine* Cells |
|---|---|---|
| DMSO Control | 46% | 0% |
| MBG-20 Antisense 50 μM | 50% | 41% |
| MBG-20-$C_2$ 50 μM | 61% | 41% |
| MBG-20-$C_6$ 50 μM | 60% | 48% |
| MBG-20-$C_{10}$ 50 μM | 62% | 66% |

*See Table I.

As shown in Table III, the results obtained indicate that the aminoalkane-terminated oligomers are more effective in producing the desired degree of selective synthesis inhibition than their cognate sequences lacking the terminal alkane. For example, the $C_{10}$ derivative was about 60% more effective than the control unmodified 20 mer in reducing the number of hemoglobin positive cells. In general, the longer the alkyl chain, the lower the concentration of oligomer required to effect the same % of inhibition.

EXAMPLE 12

The Effect of Fluorescein Terminated Oligonucleotides on the Synthesis of β-globin Protein in Cultured Cells Using the methods of synthesis provided in Example 1, 15 to 20 base long oligonucleotides conjugated to a 5'-terminal fluorescein using ethylene diamine as the linker were constructed. This material has the further advantage that uptake of the oligomer into the cells can be monitored by fluorescence microscopy which provides further evidence of the cellular fate of the product. Purified fluorescent oligomers were tested for their effectiveness in preventing the specific expression of hemoglobin in MEL cells induced to produce hemoglobin. The results are shown in Table IV. The protocol for the test is given in Example 10.

TABLE IV

THE EFFECT OF FITC CONJUGATION ON THE INHIBITION OF HEMOGLOBIN SYNTHESIS IN CULTURED CELLS

| Oligomer* | % Viable Cells | Inhibition of Benzidine* Cells |
|---|---|---|
| DMSO Control | 53% | 0% |
| MBG-20 Antisense 50 μM | 73% | 35% |
| MBG-20-$C_2$-FITC 50 μM | 68% | 45% |
| MBG-20-$C_6$-FITC 50 μM | 76% | 36% |
| MBG-20-$C_{10}$-FITC 50 μM | 72% | 52% |

*See Table I.

As shown in Table IV, the results obtained indicate that the fluorescein-terminated oligomers are at least as effective in producing selective inhibition of hemoglobin synthesis as their cognate control sequences lacking the FITC. Further, fluorescence microscopy of the treated cells showed enhanced fluorescence due to fluoresceinated oligomer uptake. These cells were then isolated, washed several times in physiological saline and lysed by freeze thawing several times in water. The resultant solution was centrifuged to remove cell debris and the amount of fluoresceinated oligomer present quantitated in an Aminco spectrofluorometer. The results obtained showed that the treated cells assimilated an average of $10^7$ molecules of fluoresceinated oligomer per cell. This is about 10 times higher than cellular uptake of similar DNA oligomers (i.e. lacking the solubility) moiety of about $10^6$ molecules per cell.

Thus it can be seen that the addition of a hydrophobic moiety, in this case fluorescein, to the oligomer results in substantially increased cellular uptake of the oligomer without affecting its ability to selectively block protein synthesis.

EXAMPLE 13

The Effect of Polyethylene Glycol Terminated Oligonucleotides on the Synthesis of β-globin Protein in Cultured Cells Using the methods of synthesis provided in the previous examples, 20 base long oligonucleotides conjugated to a 5'-terminal polyethylene glycol were constructed as described in Example 4. These molecular conjugates were purified and tested for their effectiveness in preventing the specific expression of hemoglobin as described in Example 10.

TABLE V

THE EFFECT OF POLYETHYLENE GLYCOL CONJUGATION ON THE INHIBITION OF HEMOGLOBIN SYNTHESIS IN CULTURED CELLS

| Oligomer Conjugate* | Viable Cells (% of Control) | Inhibition of Benzidine* Cells |
|---|---|---|
| DMSO Control | 33% | 0% |
| MBG-15 Antisense 100 μM | 50% | 25% |
| MB15-$C_2$ 100 μM | 60% | 22% |
| PEG(ss) 100 μM | 43% | 24% |
| MBG-20 + PEG(ss) 100 μm | 43% | 78% |
| DMSO Control | 65% | 0% |
| MBG-20-PEG(ss) 15 μM | 0% | 95% |
| 5 μM | 62% | 52% |
| 1 μM | nd | −2% |
| 0.1 μM | 64% | −5% |

*See Table I.

As shown in Table V, the results obtained show that oligomers conjugated to polyethylene glycol are more effective in producing the desired degree of selective synthesis inhibition than controls. The polyethylene glycol conjugate in this experiment was found to be approximately 10 times more active in preventing the expression of hemoglobin than the control combination of the 20 mer and polyethylene glycol. It is also interesting to note that the simple addition of polyethylene glycol to the medium increases the effectiveness of the added control antisense oligomer, in consonance with the increased effectiveness observed for the PEG conjugates.

It is evident from the above results that the novel conjugates of the subject invention provide substantial advantages in enhancing the efficiency in which transcriptional mechanisms may be modulated. In accordance with the subject invention, a wide variety of cellular, both prokaryotic and eukaryotic, as well as viral, physiological processes may be regulated. The compositions can be used in vitro and in vivo. In the former, systems can be studied, mammalian cells protected from mycoplasma, phenotypes modified, and the like. In the latter, the compositions can be used for therapy in inhibiting the proliferation of pathogens, selectively inhibiting certain classes of cells, e.g., B-cells and T-cells, or the like.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for inhibiting the maturation or translation of a messenger RNA in a cell, said method comprising:

contacting said cell with a composition comprising an oligonucleotide sequence complementary to a transcription product of said cell and a group covalently linked to said oligonucleotide sequence to provide an amphiphilic molecule, whereby said composition migrates into the cell interior resulting in the inhibition of maturation and/or translation of said transcription product.

2. A method according to claim 1, wherein said cell is in culture and said composition is introduced into the nutrient medium.

3. A method according to claim 1, wherein said oligonucleotide is of from about 6 to 30 nucleotides.

4. A method according to claim 3, wherein at least one of said oligonucleotides has a phosphate as the phosphorus moiety.

5. A method according to claim 3, wherein at least one of said oligonucleotides has a phosphonate with an alkyl group of from 1 to 3 carbon atoms as the phosphorus moiety.

6. A method according to claim 1, wherein said group is a hydrophobic aromatic group.

7. A method according to claim 1, wherein said aromatic group is a trityl group.

8. A method according to claim 7, wherein said aromatic group is a fluorescein group.

9. A method according to claim 1, wherein said group is a polyalkyleneoxy group, wherein said alkylenes are of from 2 to 10 carbon atoms.

10. A method according to claim 9, wherein said polyalkyleneoxy group is from about 6 to 200 units.

11. A cell comprising a composition comprising an oligonucleotide sequence complementary to a transcription product of said cell and an amphiphilic or hydrophobic group covalently linked to said oligonucleotide sequence to provide an amphiphilic molecule.

12. A cell according to claim 11, wherein said cell is in culture.

13. A composition of matter comprising:
an oligonucleotide sequence of at least six nucleotides complementary to a transcriptional product of a cell;
an amphiphilic group comprising a polyalkyleneoxy group, wherein said alkylenes are of from 2 to 10 carbon atoms;
a linker of at least one atom covalently bonded to said oligonucleotide sequence and to said amphiphilic group.

14. A composition of matter according to claim 13, wherein said oligonucleotide is of from about 6 to 30 nucleotides.

15. A composition of matter according to claim 13, wherein at least one of said oligonucleotides has a phosphate as the phosphorus moiety.

16. A composition of matter according to claim 13, wherein at least one of said oligonucleotides has a phosphonate with an alkyl group of from 1 to 3 carbon atoms as the phosphorus moiety.

17. A composition of matter according to claim 13, wherein said linking group includes at least one of an amino, quinone, thioether, or amide group.

18. A composition of matter according to claim 13, wherein said oligonucleotide sequence is complementary at least in part to a non-coding region.

19. A composition of matter according to claim 13, wherein said oligonucleotide sequence is complementary at least in part to a coding region.

* * * * *